United States Patent [19]

Cooper et al.

[11] 4,127,568
[45] Nov. 28, 1978

[54] PROCESS FOR 3β-AMINOAZETIDIN-2-ONES

[75] Inventors: Robin D. G. Cooper; Gary A. Koppel; Lawrence J. McShane, all of Indianapolis, Ind.

[73] Assignee: Eli Lilly and Company, Indianapolis, Ind.

[21] Appl. No.: 775,240

[22] Filed: Mar. 7, 1977

[51] Int. Cl.$^2$ .................. C07D 205/08; C07D 498/04
[52] U.S. Cl. .................. 260/239 A; 260/306.7 C; 260/307 F
[58] Field of Search .................. 260/239 A, 239 AL

[56] References Cited

U.S. PATENT DOCUMENTS 4,075,219   2/1978   McShane .................. 260/239 A

OTHER PUBLICATIONS

Sheehan et al. in "Molecular Modification of Drug Design" (ACS, 1964), p. 23.

*Primary Examiner*—Donald G. Daus
*Assistant Examiner*—Mark L. Berch
*Attorney, Agent, or Firm*—William B. Scanlon; Arthur R. Whale

[57] ABSTRACT

1-[α-(Carboxy)-4-hydroxybenzyl]-3β-aminoazetidin-2-one esters are prepared by converting 2-acyl-3,3-dialkyl-7-oxo-α-[4-(benzyloxy)phenyl]-4-thia-2,6-diazabicyclo[3.2.0]-heptane-6-acetic acid esters with mercuric acetate in an aqueous organic solvent mixture, e.g., in aqueous methanol, to 7-oxo-3-phenyl-α-[4-(benzyloxy)phenyl]-4-oxa-2,6-diazabicyclo[3.2.0]hept-2-ene-1-acetic acid esters and the latter are reacted with PCl$_5$ and pyridine to provide the monocyclic 1-[α-(carboxy)-4-benzyloxybenzyl]-3β-(α-chlorobenzylideneamino)-4-chloroazetidin-2-one esters. Reduction of the dichloro azetidin-2-one with an organo tin hydride and azobisisobutyronitrile affords the deschloro, 1-[α-(carboxy)-4-benzyloxybenzyl]-3β-benzylideneaminoazetidin-2-one ester. The latter is hydrolyzed and the 4-benzyloxy group is cleaved via catalytic hydrogenolysis to yield an ester of 1-[α-(carboxy)-4-hydroxybenzyl]-3β-aminoazetidin-2-one. The 3β-amino ester is useful for the preparation of the antibiotic FR 1923 (nocardicin).

8 Claims, No Drawings

PROCESS FOR 3β-AMINOAZETIDIN-2-ONES

BACKGROUND OF THE INVENTION

This invention is concerned with a chemical process for preparing substituted azetidin-2-ones. In particular it is concerned with a process for the preparation of certain 3β-aminoazetidin-2-ones which are useful intermediates in the synthesis of azetidin-2-one antibiotics for example the antibiotic FR 1923.

The antibiotic FR 1923, also referred to as nocardicin, has been previously described, for example in Belgium Pat. No. 830,934 and by H. Aoki et al., 15th Interscience Conference on Antimicrobial Agents and Chemotherapy, Abstract No. 97, Sept. 1975. Nocardicin has the following structural formula.

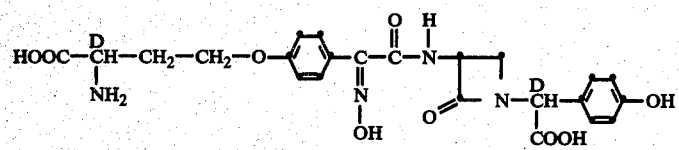

Antibiotic FR 1923 has been obtained by culturing Nocardia uniformis var. Tsuyamanensis ATCC 21806 as described by U.S. Pat. No. 3,923,977 issued Dec. 2, 1975.

This invention provides a process for preparing the "nucleus" of nocardicin represented by the following formula,

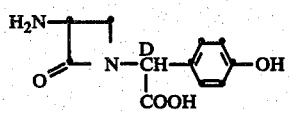

and esters and hydroxy group derivatives thereof.

The nocardicin nucleus is useful in the preparation of nocardicin via acylation with an amino-protected and esterified derivative of 4-(3-amino-3-carboxypropoxy)-phenylglyoxylic acid, the acyl side chain of nocardicin. The acylation product, a 3β-phenylglyoxamide azetidin-2-one is deblocked and de-esterified and is converted to nocardicin by formation of the oxime derivative. The synthesis of the acyl side chain of nocardicin and the amino-protected esters thereof is described in co-pending application Ser. No. 739,160 now abandoned filed Nov. 5, 1976 and its continuing application Ser. No. 825,344 filed Aug. 17, 1977.

DETAILED DESCRIPTION

According to the process of this invention, the fused bicyclic "thiazolidine-azetidinone" represented by the formula 1

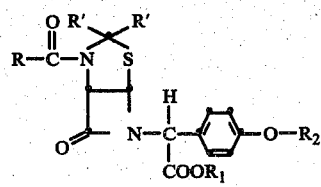

wherein R is $C_1$–$C_3$ alkyl, phenyl, or benzyl; both of R' are methyl or ethyl; $R_1$ is methyl, benzyl, 4-methoxybenzyl, or diphenylmethyl; and $R_2$ is benzyl, 4-methoxybenzyl, or diphenylmethyl; is reacted with mercuric acetate in an aqueous organic solvent to provide the fused bicyclic "oxazoline-azetidinone" represented by the formula 2.

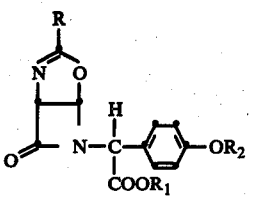

wherein R, $R_1$, and $R_2$ have the same meanings as defined above.

The oxazoline-azetidinone is reacted with phosphorus pentachloride in the presence of pyridine to effect the opening of the oxazoline ring and provide the chlorinated 3β-iminoazetidin-2-one represented by the formula 3.

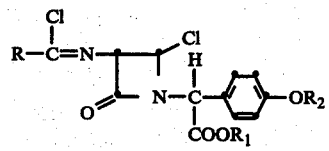

Reduction of (3) via a free radical reduction with an organotin hydride, eg. a trialkyltin hydride, and azobisisobutyronitrile affords the des chloro-imino-azetidin-2-one represented by the formula 4.

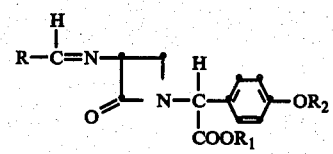

The 3β-iminoazetidin-2-one (4) is hydrolyzed to the 3β-aminoazetidin-2-one represented by the formula 5.

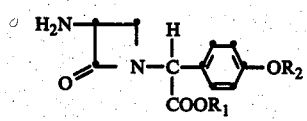

The thiazolidine azetidinone represented by the formula 1 which is the starting material employed in the process of this invention is named formally as a 2-acyl-3,3-dimethyl (or diethyl)-7-oxo-α-[4-(benzyloxy, p-methoxybenzyloxy or diphenylmethyloxy)phenyl]-4-thia-2,6-diazabicyclo[3.2.0]heptane-6-acetic acid, methyl, benzyl, 4-methoxybenzyl, or diphenylmethyl ester. For convenience of description, the compounds represented by the formula 1 are referred to herein as thiazolidine-azetidinones. The preparation of these thiazolidine-azetidinones will be described hereinafter.

In carrying out the process of this invention, the thiazolidine-azetidinone is reacted with mercuric acetate in an aqueous water-miscible organic solvent at a temperature between about 25° C. and about 100° C. to form the oxazoline-azetidinone represented by the formula 2. Between about 1 mole and about 4 moles of mercuric acetate per mole of thiazolidine azetidinone is a suitable ratio of reactants, although excess amounts of mercuric acetate can be used. Preferably, 2 moles of mercuric acetate per mole of starting material are used.

Water-miscible organic solvents which can be used include the ethers such as tetrahydrofuran, dioxane, and the dimethyl ether of ethylene glycol; the lower alcohols such as methanol and ethanol; and the nitriles such as acetonitrile. The amount of water in solution with the organic solvent is not critical and in general between about 10 percent and about 60 percent water by volume is a suitable amount. The preferred aqueous solvent is aqueous tetrahydrofuran containing between about 10 and 60 percent water.

The reaction can be carried out at room temperature or with heating at steam bath temperatures.

In performing the process of this invention, it is preferable to obtain the oxazoline-azetidinone relatively free of contaminants prior to its use in the succeeding step of the process. Accordingly, following the reaction, the reaction mixture is filtered to remove insolubles and the filtrate is extracted with a water immiscible organic solvent. Solvents such as ethyl acetate, amyl acetate, chloroform, or methylene chloride are suitable extractants. The extract is washed, dried, and evaporated to provide the oxazoline-azetidinone as a residue suitable for use in the next reaction of the process. Alternatively, the product can be obtained in crystalline form by crystallization from a suitable solvent such as diethyl ether.

The oxazoline-azetidinone formed as product in the above-described reaction is represented by the foregoing formula 2 and is formally named a 7-oxo-3-alkyl(-phenyl or benzyl)-$\alpha$-[4-benzyloxy, p-methoxybenzyloxy or diphenylmethyloxy)phenyl]-4-oxa-2,6-diazabicyclo[3.2.0]hept-2-ene-1-acetic acid, methyl, benzyl, 4-methoxybenzyl, or diphenylmethyl ester.

The oxazoline-azetidinone obtained as described above is chlorinated with a phosphorus or antimony chloride to provide the dichloro compound, a 1-[$\alpha$-(benzyloxycarbonyl, methoxycarbonyl, 4-methoxycarbonyl, or diphenylmethoxycarbonyl)-4-benzyloxy, 4-methoxybenzyloxy, or diphenylmethoxybenzyl]-3$\beta$-($\alpha$-chloroimino)-4$\alpha$-chloroazetidin-2-one represented by the foregoing formula 3.

The chlorination is carried out under anhydrous conditions with phosphorus pentachloride or phosphorus trichloride in an inert solvent. Antimony tri or pentachloride can also be used as the chlorinating agent, however, phosphorus pentachloride is preferred. The chlorination can be carried out at a temperature between about −10° C. and about 45° C. and preferably at room temperature of about 20°–25° C.

"Inert solvents" are solvents which are unreactive under the chlorination conditions of the process, for example, the chlorinated hydrocarbon solvents such as chloroform, methylene chloride, dichloroethane, and trichloroethane are suitable inert solvents.

The reaction is carried out in the presence of a tertiary organic amine which serves as a hydrogen chloride acceptor. Tertiary amines such as pyridine, the methylated pyridines, quinoline, or the tertiary alkylamines, for example, triethylamine can be used. Pyridine is preferred.

The phosphorus or antimony chloride is employed in excess, for example, between about a tenth molar and 2 molar excess per mole of oxazoline-azetidinone. The tertiary amine, for example, the preferred pyridine is employed in an amount equimolar with the phosphorus or antimony chloride.

The reaction is carried out by adding the chloride to a solution of the oxazoline-azetidinone in the inert solvent. The tertiary amine is added and the reaction mixture is agitated by stirring or shaking until the reaction is completed. The dichloro product is recovered by diluting the reaction mixture with water or brine below room temperatures and preferably about 0°–5° C. and separating the organic layer containing the product. The organic layer is washed, dried, and evaporated to provide the dichloro product as a residue. The product can be further purified; however, further purification is unnecessary in the process of this invention.

The 3$\beta$-($\alpha$-chloroimino)-4$\alpha$-chloroazetidin-2-one, product of the chlorination, is subjected to reduction with an organo tin hydride under free radical reduction conditions initiated with azobisisobutyronitrile. The reduction effects the replacement of both chlorine atoms with hydrogen atoms to provide the des chloro azetidin-2-one reduction product, a 1-[$\alpha$-(methyl, benzyl, 4-methoxybenzyl, or diphenylmethoxycarbonyl)-4-benzyloxy, 4-methoxybenzyloxy, or diphenylmethoxybenzyl]-3$\beta$-benzylidene (or alkylidene)aminoazetidin-2-one represented by the formula 4.

The reduction is carried out in an inert solvent under essentially anhydrous conditions. Aromatic hydrocarbon solvents such as benzene, toluene, and the xylenes provide a suitable medium for the reaction. Toluene is a preferred solvent.

Organo tin hydrides which can be employed in the process are represented by the following formula

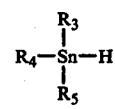

wherein $R_3$, $R_4$, and $R_5$ independently are $C_1$–$C_4$ alkyl, phenyl, or phenyl substituted by methyl or chloro.

Examples of such tin hydrides are the trialkyl tin hydrides such as tri(n-butyl)tin hydride, tin(n-propyl)tin hydride, trimethyltin hydride, and triethyltin hydride; the triaryltin hydrides such as triphenyltin hydride, and tri(p-tolyl)tin hydride; and the mixed alkyl and mixed alkyl aryltin hydrides such as di(n-butyl)phenyltin hydride, dimethylethyltin hydride, and diphenylmethyltin hydride.

A preferred tin hydride is tri(n-butyl)tin hydride.

The organo tin hydride is employed in a molar ratio of 2:1, i.e., 2 moles of organo tin hydride per mole of 3$\beta$-($\alpha$-chloroimino)-4$\alpha$-chloroazetidin-2-one. A slight excess of the tin hydride can be used without deleterious effect on the reaction product and may be used where trace amounts of water may be present.

The azobisisobutyronitrile, formally named 2,2'-azobis(2-methylpropionitrile) and represented by the following structural formula

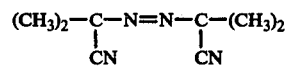

is employed in the reduction in an amount equimolar with the tin hydride.

The reaction is carried out at a temperature between about 65° C. and about 85° C. and preferably at about 70° C.

The reaction is performed by adding the organo tin hydride and the azobisisobutyronitrile to a solution of the 3β-(α-chlorobenzylideneamino) or 3β-(α-chloroalkylideneamino)-4α-chloroazetidin-2-one in the dry aromatic hydrocarbon, for example, toluene at or about room temperature. Freshly distilled solvents are preferred. After addition is complete, the reaction mixture is heated to a temperature between about 65° C. and about 85° C. with stirring. During the reaction, it is preferable to exclude atmospheric moisture by maintaining the mixture in an atmosphere of nitrogen. The course of the reaction can be followed by thin layer chromatography. When the reaction is complete, the mixture is diluted with an organic water-immiscible solvent such as ethyl acetate and is washed with dilute base and water, is dried, and evaporated to provide the 3β-benzylideneaminoazetidin-2-one or alkylideneaminoazetidin-2-one (formula 4). The product can be obtained crystalline from a suitable solvent, for example, toluene or benzene, on cooling.

In the last step of the process of this invention, the 3β-iminoazetidin-2-one is converted under acidic conditions to the 3β-aminoazetidin-2-one represented by the formula 5. The 3β-benzylideneaminoazetidin-2-one or 3β-alkylideneaminoacetidin-2-one employed in the acid removal of the benzal or alkylidene group can be purified crystalline material obtained in the organo tin hydride reduction step or crude material. In the final step of the process, it is preferable to employ the crude 3β-benzylideneamino (or alkylideneamino)azetidin-2-one obtained in the tin hydride reduction as described above. The 3β-aminoazetidinone (5) is obtained as the salt formed with the acid employed.

Acids which can be used include the mineral acids such as hydrochloric acid, sulfuric acid, or phosphoric acid and the organic sulfonic acids such as the lower alkylsulfonic acids, for example, methanesulfonic acid, ethanesulfonic acid, and propanesulfonic acid; the aromatic sulfonic acids such as benzenesulfonic acid, the toluenesulfonic acids, and α or β-naphthylenesulfonic acid. Preferred acids are hydrochloric acid and p-toluenesulfonic acid.

In carrying out the reaction, the 3β-iminoazetidin-2-one (4) is dissolved in a water immiscible organic solvent such as an ester, for example, ethyl acetate or amyl acetate; a chlorinated hydrocarbon, for example, methylene chloride or trichloroethane; and the solution is shaken with excess hydrochloric acid, e.g., 1N-hydrochloric acid. The organic phase is separated, dried, and evaporated to dryness to provide the 3β-aminoazetidin-2-one (5) hydrochloride. The product can be purified by trituration with petroleum ether or by recrystallization.

Alternatively, the benzal or alkylidene group of (4) can be removed to provide the 3β-aminoazetidin-2-one in the following manner. The crude tin hydride reduction product (4) is dissolved in diethyl ether and the solution is cooled to about 0°–5° C. in an ice-water mixture. Hydrogen chloride is bubbled through the cold solution with stirring. The solution is then allowed to warm to room temperature with continued stirring. The solution is evaporated to dryness in vacuo and the residue of 3β-aminoazetidinone hydrochloride is purified by trituration with diethyl ether or petroleum ether.

Preferably, in the process of this invention, crude (4) is converted to (5) with p-toluenesulfonic acid. For example, (4) is dissolved in ethyl acetate or other suitable solvent and a slight excess of p-toluenesulfonic acid monohydrate is added to the solution. The benzal group is rapidly removed as shown by the disappearance of the imine via thin layer chromatography (silica gel, benzene:ethyl acetate, 7:3). On standing, or with cooling, the p-toluenesulfonic acid salt of the 3β-aminoazetidin-2-one forms as a crystalline precipitate.

The 3β-aminoazetidin-2-one salts are readily converted to the 3β-amino compound (5) as the free amine as follows. The salt is dissolved in a suitable water immiscible solvent, for example, ethyl acetate and the solution is shaken vigorously with an aqueous solution of a base such as sodium or potassium bicarbonate or sodium or potassium carbonate. The organic layer is separated, dried, and evaporated to provide the free amine (5) as a residue. The 3β-aminoazetidin-2-one obtained is generally of sufficient quality for use in the preparation of nocardicin as described hereinafter. Thus, in the process of this invention, the crude organo tin hydride reduction product (4) is converted to the 3β-amino compound (5) via the acid salt. The direct preparation of the salt form provides for the purification of the 3β-aminoazetidin-2-one nucleus (5). Should further purification of (5) be necessary, it can be achieved by chromatography over silica gel.

Representative of the 3β-aminoazetidin-2-ones provided by the process of this invention are 1-[α-(benzyloxycarbonyl)-4-benzyloxybenzyl]-3β-aminoazetidin-2-one, 1-[α-(methoxycarbonyl)-4-benzyloxybenzyl]-3β-aminoazetidin-2-one, 1-[α-(4-methoxybenzyloxycarbonyl)-4-benzyloxybenzyl]-3β-aminoazetidin-2-one, 1-[α-(diphenylmethoxycarbonyl)-4-diphenylmethoxybenzyl]-3β-aminoazetidin-2-one, 1-[α-(4-methoxybenzyloxycarbonyl)-4-diphenylmethyloxybenzyl]-3β-aminoazetidin-2-one and 1-[α-(diphenylmethoxycarbonyl)-4-benzyloxybenzyl]-3β-aminoazetidin-2-one.

As mentioned previously, the starting material employed in the process is the bicyclic thiazolidine-azetidinone represented by the foregoing formula 1. The thiazolidine-azetidinone is prepared as described in copending application Ser. No. 739,161 filed Nov. 5, 1976.

According to the described process a 2,2-dialkyl-3-acylthiazolidine-4-carboxylic acid having the L-configuration is reacted with an ester of a 4-hydroxy-protected D-phenylglycine to obtain the corresponding amide (A) as shown in the following reaction scheme.

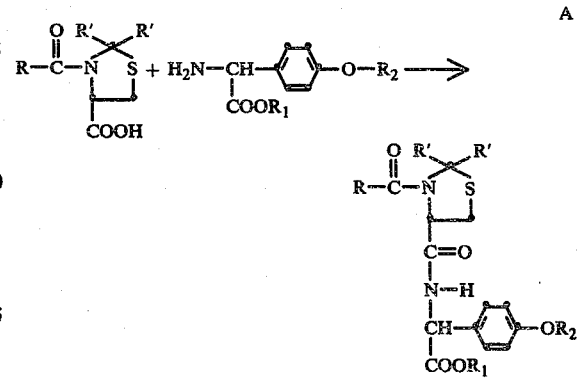

In the above formulas R, $R_1$, $R_2$, and R' have the same meanings as previously defined.

The preparation of the amide (A) is carried out by reacting the active ester of the thiazolidine-4-carboxylic acid formed with 1-hydroxybenzotriazole with the esterified and hydroxy-protected phenylglycine in the presence of dicyclohexylcarbodiimide.

The thiazolidine amide (A) is converted to the cyclic thiazolidine-azetidinone represented by the formula 1 as shown in the following scheme.

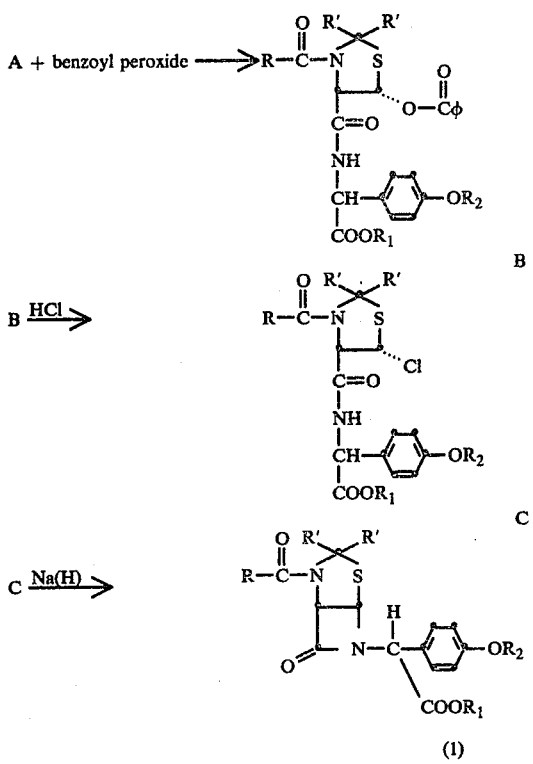

As shown in the above reaction scheme, the thiazolidine amide is first converted to the 5α-benzoate derivative (B) by reacting (A) with benzoyl peroxide. The reaction is carried out by heating the amide in an inert solvent with benzoyl peroxide. Suitable solvents include the hydrocarbon solvents such as benzene and toluene, or the chlorinated hydrocarbon solvents such as methylene chloride and chloroform. An excess of benzoyl peroxide is employed and preferably between about a 2 and 4 molar excess.

The 5α-benzoate (B), which can be purified and separated from unreacted starting material by chromatography over silica gel, is then reacted with hydrogen chloride in an inert solvent at a temperature between about −20° and 0° C. to form the corresponding 5α-chloro thiazolidine amide represented by the above formula C. The reaction is conveniently carried out in a chlorinated hydrocarbon solvent such as methylene chloride or chloroform and the progress of the reaction can be followed by thin layer chromatography.

The 5α-chloro compound (C) on treatment under anhydrous conditions with a strong base such as sodium hydride or 1,5-diazabicyclo[5.4.0]-undec-5-ene (DBU) undergoes cyclization to form the bicyclic thiazolidine-azetidinone represented by the formula 1.

The cyclization to form (1) is carried out at a temperature between about 0° and 30° C. in an inert solvent. Suitable solvents include those previously mentioned in connection with the foregoing reactions, for example, the halogenated hydrocarbon solvents such as chloroform, methylene chloride, and trichloroethane. The product (1) of the cyclization is best purified for use in this process by chromatography over silica gel. Gradient elution employing a gradient of benzene to benzene-ethyl acetate (7:3, v:v) is a suitable chromatographic system for the purification of compound (1).

The 3-acylthiazolidine-4-carboxylic acid is prepared by heating excess acetone or diethyl ketone with L-cysteine at the reflux temperature.

In a preferred embodiment of this invention, the thiazolidine-azetidinone represented by the foregoing formula 1 wherein R is phenyl, each of R' is methyl, and $R_1$ and $R_2$ are both benzyl, is reacted with mercuric acetate in tetrahydrofuran containing 50 percent by volume of water to form the oxazoline-azetidinone represented by the formula 2 wherein R is phenyl and both $R_1$ and $R_2$ are benzyl. The oxazoline-azetidinone is chlorinated at about 20°–25° C. with phosphorus pentachloride in methylene chloride in the presence of pyridine to form the correspondingly substituted 3β-(α-chlorobenzylideneamino)-4α-chloroazetidin-2-one represented by the formula 3 wherein R is phenyl and $R_1$ and $R_2$ are both benzyl. The dichloro product is reduced in toluene at about 70° C. with tri(n-butyl)tin hydride and azobisisobutyronitrile to provide the deschloro reduction product. Without purification the crude deschloro reduction product, 1-[α-(benzyloxycarbonyl)-4-benzyloxybenzyl]-3β-benzylideneaminoazetidin-2-one, is dissolved in ethyl acetate and the solution treated with p-toluenesulfonic acid monohydrate to precipitate as the p-toluenesulfonate salt, 1-[α-(benzyloxycarbonyl)-4-benzyloxybenzyl]-3β-aminoazetidin-2-one represented by the formula 5 wherein both $R_1$ and $R_2$ are benzyl. The tosylate salt of the nucleus ester is treated in ethyl acetate with a dilute aqueous solution of sodium bicarbonate to form the 3β-amino nucleus ester represented by the following formula

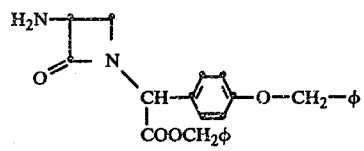

The 3β-aminoazetidin-2-one ester represented by the formula 5 possesses a center of asymmetry at the α-carbon attached to the nitrogen atom of the azetidine ring. The compound in the D-configuration is preferred. Accordingly, in carrying out the process of this invention, the thiazolidine-azetidinone starting material represented by the formula 1 having the D-configuration is employed.

During the preparation of the thiazolidine-azetidinone starting material as described above, the cyclization reaction of C to form the bicyclic thiazolidine-azetidinone (1), epimerization can occur. For example, the 2,2-dialkyl-3-acyl-5-chlorothiazolidine-4-carboxamide (C) prepared with D-phenylglycine affords C having the D-configuration. Cyclization of C to 1 is accompanied by epimerization at the asymmetric center resulting in the preparation of (1) as a mixture of D and L isomers. The desired D-isomer can be separated from the L-isomer by fractional crystallization. For example, a solution of the mixture of isomers in ethyl acetate on cooling and standing first deposits crystals of the less soluble D-isomer and the filtrate on dilution with petroleum ether affords a crystalline precipitate of the L-isomer.

The process of this invention provides the hydroxy-protected and esterified nocardicin nucleus 5, which is useful in the synthesis of nocardicin. Accordingly, the 3β-aminoazetidin-2-one ester 5 is acylated with an amino-protected ester of 4-(D-3-amino-3-carboxypropoxy)phenylglyoxylic acid O-acyl oxime to form the amino-, carboxy and hydroxy-protected nocardicin as illustrated in the following reaction scheme.

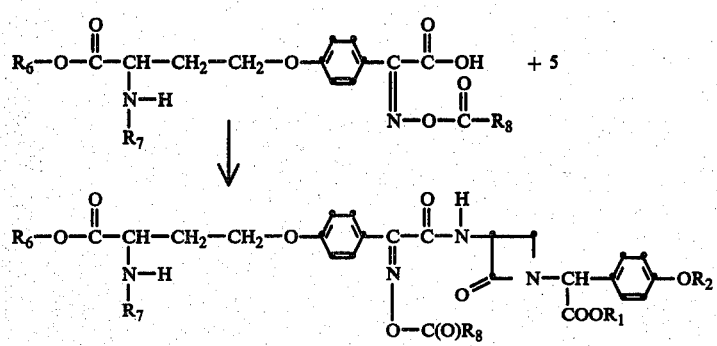

$R_6$ represents a carboxylic acid-protecting group which is readily removable under acidic conditions for example diphenylmethyl, benzyl, 4-methoxybenzyl, 2,4,6-trimethylbenzyl, or phthalimidomethyl; $R_7$ represents an amino-protecting group for example, the t-butyloxycarbonyl group; $R_1$ and $R_2$ have the same meanings as previously defined herein; and $R_8$ is acetyl, chloroacetyl or dichloroacetyl.

The above depicted acylation to form the FR 1923 precursor can be carried out by coupling the glyoxylic acid O-acyl oxime with the free 3β-amino nucleus compound (5) with a condensing agent such as a carbodiimide or by forming a mixed anhydride of the acid and reacting the anhydride with the 3β-amino nucleus in the presence of triethylamine.

The preferred acylation method is the former wherein the acid is condensed with the amine nucleus with the aid of a condensing agent. For example, the 3β-amino nucleus ester (5) is reacted in an inert solvent such as methylene chloride or tetrahydrofuran with the amino-protected and carboxy-protected phenylglyoxylic acid O-acetyl oxime in the presence of an equimolecular amount or a small excess of a carbodiimide such as dicyclohexylcarbodiimide. The reaction mixture is maintained substantially anhydrous for best results. The reaction is carried out with stirring at about room temperature. After the reaction is complete, the insoluble dicyclohexylurea is filtered and the protected nocardicin is recovered from the filtrate.

The protected nocardicin is deblocked to provide nocardicin. For example, the protected nocardicin of the above formula wherein $R_1$ and $R_2$ are benzyl, $R_6$ is diphenylmethyl, $R_7$ is the t-butyloxycarbonyl (BOC) amino-protecting group, and $R_8$ is acetyl, is first reacted with trifluoroacetic acid at about room temperature to effect the removal of the diphenylmethyl ester group $R_6$, the BOC group $R_7$, and the O-acetyl group of the oxime. Thereafter the benzyl groups $R_1$ and $R_2$ are removed by treatment of the partially de-blocked molecule with aluminum chloride in an inert solvent containing anisole.

Alternatively the acylation can be carried out with a mixed anhydride of the phenylglyoxylic acid. Suitable mixed anhydrides can be prepared with methyl chloroformate or isobutyl chloroformate. The acylation of the amino nucleus ester (5) is carried out at about 5° to about 25° C. with stirring in a suitable solvent such as methylene chloride or tetrahydrofuran in the presence of a tertiary amine preferably triethylamine. The reaction is carried out under substantially anhydrous conditions.

The acylation product is next converted to the oxime via reaction with hydroxylamine hydrochloride in an inert aqueous solvent in the presence of a hydrogen halide acceptor to provide the esterified and amino-protected nocardicin. Following the formation of the oxime, the ester groups $R_6$ and $R_1$, the amino-protecting group $R_7$, and the hydroxyl-protecting group $R_2$ are removed to provide the antibiotic nocardicin.

The amino-protected and esterified phenylglyoxylic acid is prepared by the method described in co-pending application Ser. No. 739,160, filed Nov. 5, 1976. As described therein an amino-protected salt of D-methionine of the formula

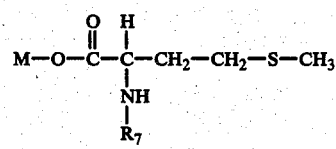

for example the salt wherein M is dicyclohexylammonium and $R_7$ is as previously defined herein, is converted to the trimethylsilyl ester and is alkylated on the sulfur atom with an alkyl or benzyl iodide, for example methyl iodide and the alkylsulfonium iodide of the formula

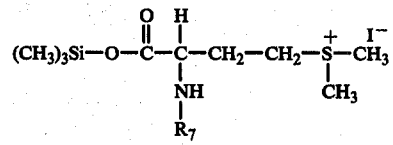

is reacted in an inert solvent with potassium t-butoxide to form the cyclic amino-protected D-homoserine lactone of the formula

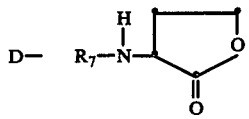

The lactone is hydrolyzed with an alkali metal hydroxide to the amino-protected D-homoserine alkali metal salt of the formula

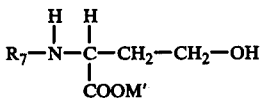

wherein M' is sodium or potassium, and the latter is esterified e.g., with diphenylmethyl bromide. The esterified D-homoserine is then coupled with a 4-hydroxyphenylglyoxylic acid ester, for example, the p-nitrobenzyl ester, the coupling reaction being carried out with a trialkyl or triarylphosphine, and preferably triphenylphosphine, and diethyl azodicarboxylate to form the amino-protected diester of the formula

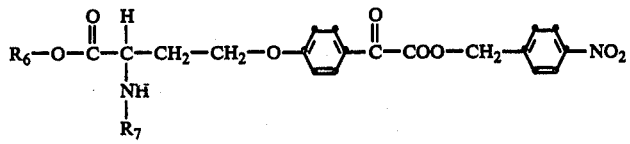

The p-nitrobenzyl ester group is selectively de-esterified by reduction methods whereby the other ester $R_6$, which is selected from among the acid-labile ester groups, remains substantially intact. For example, the p-nitrobenzyl ester group is removed via reduction with sodium sulfide. The ester group $R_6$ which is an acid sensitive group such as the diphenylmethyl group remains unaffected under the reduction conditions. The selective de-esterification product, the phenylglyoxylic acid, is represented by the formula

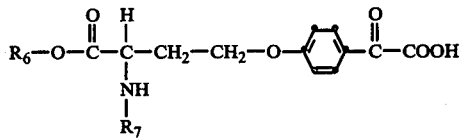

In a further aspect of this invention the oxazoline-azetidinone intermediate (2) is prepared by reacting a 3-acylamino-4α-acetoxyazetidin-2-one ester represented by the formula

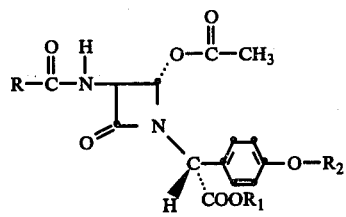

in an inert solvent with hydrogen chloride.

In the foregoing formula R, $R_1$, and $R_2$ have the same meanings as defined hereinabove.

The reaction is carried out at a temperature between about −10° C. and about 25° C., preferably at about 0° C. Inert solvents which can be used are the halogenated hydrocarbon solvents such as chloroform, methylene chloride, dichloroethane, and trichloroethane.

The reaction is carried out by passing hydrogen chloride into a solution of the 3-acyl-4α-acetoxyazetidinone ester until excess hydrogen chloride is present. Generally, the solution is saturated with the gas for best results. Preferably, the reaction is carried out at about 0° C. to about 5° C.

The oxazoline-azetidinone product is recovered by conventional isolation procedures. For example, the reaction mixture is evaporated to dryness and the residue containing the crude product is dissolved in ethyl acetate. The solution is washed with a dilute base such as a dilute solution of sodium bicarbonate, is dried and optionally treated with carbon, and evaporated to dryness to obtain the oxazoline-azetidinone.

In a preferred embodiment of this aspect of the invention, the 3-benzoylamino-4α-acetoxyazetidinone represented by the above formula wherein R is phenyl, and $R_1$ and $R_2$ are both benzyl is dissolved in methylene chloride and the solution is saturated with hydrogen chloride at a temperature of 0° C. to provide the oxazoline-azetidinone represented by the formula 2 wherein R is phenyl and $R_1$ and $R_2$ are both benzyl.

The 3-acylamino-4α-acetoxyazetidinone ester represented by the foregoing structural formula is prepared according to the method described by co-pending application Ser. No. 753,980 filed Dec. 23, 1976. As described therein a thiazolidine-azetidinone represented by the above formula (1) is reacted in acetic acid with mercuric acetate to form a 3-(N-propenylacylamino)-4α-acetoxyazetidinone ester represented by the formula

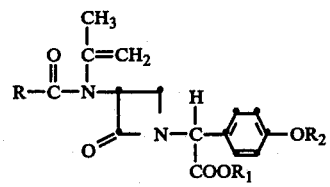

The N-propenylamide is then reacted in a water miscible solvent with a dilute mineral acid such as dilute hydrochloric acid to effect the hydrolysis of the propenyl group to provide the 3-acylamino-4α-acetoxyazetidinone ester.

In a further aspect of this invention, certain novel compounds are provided which are useful in the process of this invention for the synthesis of nocardicin. One group of such compounds are the previously described oxazoline-azetidinones represented by the formula 2. Preferred compounds are represented when in the formula 2, R is phenyl, $R_1$ is benzyl or diphenylmethyl, and $R_2$ is benzyl or diphenylmethyl. An especially preferred compound is represented by the formula 2 when R is phenyl and both $R_1$ and $R_2$ are benzyl.

Another group of novel compounds which are useful intermediates in the process of this invention are the dichloro and deschloroazetidin-2-ones represented by the formula

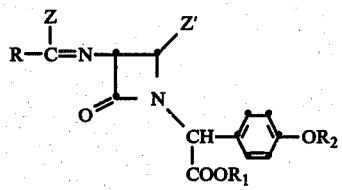

wherein R, $R_1$, and $R_2$ have the same meanings as previously defined herein and Z and Z' are both hydrogen or chloro.

Examples of compounds represented by the above formula are 1-[α-(benzyloxycarbonyl)-4-benzyloxybenzyl]-3β-benzylideneaminoazetidin-2-one, 1-[α-(diphenylmethoxycarbonyl)-4-diphenylmethoxybenzyl]-3β-benzylideneaminoazetidin-2-one, 1-[α-(methoxycarbonyl)-4-benzyloxybenzyl]-3β-ethylideneaminoazetidin-2-one, 1-[α-(benzyloxycarbonyl)-4-benzyloxybenzyl]-3β-phenethylideneaminoazetidin-2-one, 1-[α-(benzyloxycarbonyl)-4-benzyloxybenzyl]-3β-(α-chlorobenzylideneamino)-4α-chloroazetidin-2-one, and 1-[α-(diphenylmethoxycarbonyl)-4-diphenylmethoxybenzyl]-3β-(α-chlorobenzylideneamino)-4α-chloroazetidin-2-one.

Preferred compounds of the above formula are those having the D-configuration. A further preferred group is represented when R is phenyl and $R_1$ and $R_2$ are benzyl or diphenylmethyl. An especially preferred intermediate of the above formula is represented when R is phenyl and both $R_1$ and $R_2$ are benzyl.

The following examples are provided to further illustrate the process of this invention and the preparation of the intermediates useful therein, and are not intended to limit the scope of this invention.

The abbreviations used in the examples refer to the following: φ=phenyl, TLC=thin layer chromatography, TMS=tetramethylsilane, BOC=-t-butyloxycarbonyl, T60=Varian Associates Model T60 Nuclear Magnetic Spectrometer, and in the description of the nuclear magnetic spectra, s=singlet, d=doublet, m=multiplet, q=quartet, and t=triplet.

EXAMPLE 1

Preparation of 1-[α-(benzyloxycarbonyl)-4-benzyloxybenzyl]-3β-aminoazetidin-2-one To a stirred solution of 2.29 g. of 2-benzoyl-3,3-dimethyl-7-oxo-α-[4-(benzyloxy)phenyl]-4-thia-2,6-diazabicyclo[3.2.0]heptane-6-acetic acid benzyl ester in 230 ml. of tetrahydrofuran and 230 ml. of water were added 4.58 g. of mercuric acetate. The mixture was stirred at room temperature for three hours and was filtered with the aid of talc. The filtrate was extracted with ethyl acetate, the extract dried, treated with carbon, and then was evaporated to provide the reaction product as a crude oil. The oil was dissolved in the minimum amount of diethyl ether and the solution was seeded with a few crystals of the product. The product, 7-oxo-3-phenyl-α-[4-(benzyloxy)phenyl]-4-oxa-2,6-diazabicyclo[3.2.0]-hept-2-ene-1-acetic acid, benzyl ester, crystallized from solution. The product was filtered and dried. The yield of first crop product was 1.03 g. while an additional 0.24 g. of product contaminated with a residue was obtained from the filtrate. The NMR spectrum of the first crop of product was in agreement with the following structural formula of the oxazoline-azetidinone product.

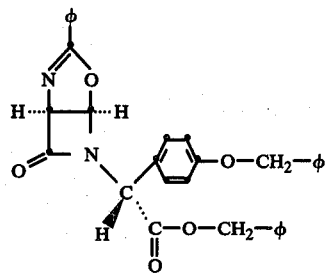

NMR (CDCl₃, TMS): 5.00 (s, $CH_2$); 5.20 (s, $CH_2$), 5.30 (d, CH), 5.50 (s, CH), 6.30 (d, CH) and 6.70-7.75 (m, aromatic H) delta.

The oxazoline-azetidinone product (500 mg., 0.95 mmole of first crop material) was dissolved in 100 ml. of dry methylene chloride maintained under nitrogen and 600 mg. (2.90 mmole) of phosphorus pentachloride were added to the solution with stirring. Next, 0.23 ml. of pyridine were added and the reaction mixture was stirred at room temperature for 1.5 hours. The reaction was followed by TLC on silica gel using benzene:ethyl acetate (7:3, v:v). After 1.5 hours almost all of the starting material had reacted and the product occurred on the TLC as faster moving material having an Rf of about 0.9.

The reaction mixture was cooled in an acetone-dry ice bath and poured into ice cold brine. The methylene chloride layer was separated, washed with cold brine, dried, treated with carbon and then evaporated to yield 480 mg. of 1-[α-(benzyloxycarbonyl)-4-benzyloxybenzyl]-3β-(α-chlorobenzylideneamino)-4α-chloroazetidin-2-one as a white foam. The NMR spectrum of the product was in agreement with the structural formula of the product.

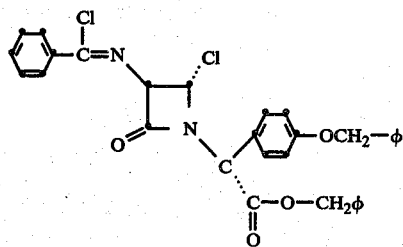

NMR (CDCl₃, TMS): 5.02 (s, $CH_2$), 5.24 (s, $CH_2$), 5.36 (s, CH), 5.42 (d, CH), 5.58 (d, CH), and 6.82-8.08 (m, aromatic H) delta.

The dichloro product (480 mg., 0.845 mmole) was dissolved in 10 ml. of freshly distilled dry toluene and 0.423 ml. (1.69 mmole) of tri-(n-butyl)tin hydride and 280 mg. (1.69 mmole) of azobisisobutyronitrile were added. The reaction mixture was stirred for about one hour at a temperature of about 70° C. The mixture was cooled and was diluted with ethyl acetate. The mixture was then washed successively with an aqueous solution of sodium bicarbonate, brine, and water and was dried. After treatment with carbon, the mixture was evaporated to dryness and the residue triturated with petroleum ether and filtered. The crude residue (485 mg.) was dissolved in toluene and refrigerated. A crystalline impurity was filtered and the filtrate was evaporated to dryness to yield 350 mg. of the des chloroazetidinone represented by the following formula.

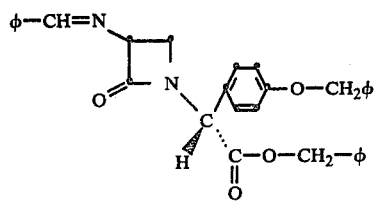

NMR (CDCl₃, TMS): 3.31 (q, CH), 3.98 (t, CH), 4.98 (s, CH₂), 5.17 (s, CH₂), 4.80 (q, CH), 5.67 (s, CH), 6.80–7.80 (m, aromatic H), and 8.33 (s, CH) delta.

The des chloroazetidinone product (350 mg.) was dissolved in 100 ml. of ethyl acetate and the solution as shaken vigorously with 30 ml. of 1N hydrochloric acid. The organic phase was separated, dried, treated with carbon and evaporated to dryness. The residue was triturated with petroleum ether and filtered to yield 1-[α-(benzyloxycarbonyl)-4-benzyloxybenzyl]-3β-aminoazetidin-2-one hydrochloride.

The hydrochloride salt was dissolved in ethyl acetate and the solution was shaken vigorously with an aqueous solution of sodium bicarbonate. The organic layer was separated, dried, treated with carbon, and evaporated to dryness. The residue was dissolved in benzene and chromatographed twice over silica gel with a benzene → ethyl acetate gradient to yield 100 mg. of the 3β-aminoazetidinone.

NMR (CDCl₃, TMS): 1.67 (s, NH₂), 2.80 (m, CH), 3.86 (m, CH), 4.21 (m, CH), 5.06 (s, CH₂), 5.18 (s, CH₂), 5.59 (s, CH), and 6.80–7.40 (m, aromatic H) delta.

EXAMPLE 2

Preparation of Nocardicin

To a solution of 100 mg. (0.24 mmole) of 1-[α-(benzyloxycarbonyl)-4-benzyloxybenzyl]-3β-aminoazetidin-2-one in 10 ml. of dry methylene chloride were added 142 mg. (0.24 mmole) of 4-[3-(t-butyloxycarbamido)-3-(diphenylmethoxycarbonyl)propoxy]-phenylglyoxylic acid O-acetyloxime and 49.5 mg. (0.24 mmole) of dicyclohexylcarbodiimide and the solution was stirred for 4 hours at room temperature. The reaction mixture was filtered, evaporated in vacuo and 60 mg. of the product were isolated by preparative thin layer chromatography over silica gel using benzene:ethyl acetate, 1:1, v:v. The acylation product is represented by the following formula.

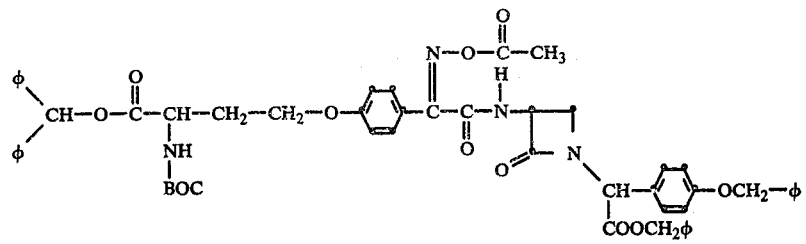

The acylation product, 60 mg., was dissolved in 2 ml. of trifluoroacetic acid and after the solution was shaken for 2 minutes at room temperature, it was evaporated in vacuo. The residue was triturated with diethyl ether and 36 mg. of the partially deblocked product, 3β-[4-(3-amino-3-carboxypropoxy)-2-hydroximino-2-phenylacetamido]-1-[α-(benzyloxycarbonyl)-4-benzyloxybenzyl]azetidin-2-one, were obtained.

The partially deblocked product, 36 mg., was dissolved in 2 ml. of dry methylene chloride with stirring and the solution was cooled to a temperature of about 0° C. A mixture of 51 mg. of aluminum chloride (0.045 mmole), 48 mg. of anisole (0.415 mmole) and 2 ml. of nitromethane was added dropwise to the cold solution. After 15 minutes the reaction mixture was allowed to warm to room temperature and the methylene chloride and nitromethane were evaporated off in vacuo at room temperature. Water (14 ml.) was added to the concentrate and the pH adjusted to 6.9 with an aqueous solution of sodium bicarbonate. The aqueous solution was desalted via column chromatography over charcoal (Pittsburgh 12–40 mesh). The column was first eluted with 100 ml. of water to collect fractions 1–14 and then with 200 ml. of water:acetone:ammonium hydroxide, 100:100:1, v:v, to collect fractions 15–50. The fractions were lyophilized.

| Fractions | Weight | Product |
|---|---|---|
| 1–14 | 135 mg. | salts |
| 16–20 | 8 mg. | nocardicin |
| 21–50 | 9.5 mg. | impure nocardicin |

Bioautographs run with the nocardicin product obtained showed the product to be identical with authentic nocardicin. The detecting microorganisms used on the bioautographs were *Serratia marcescens* and *Bacillus steriothermophilus*.

EXAMPLE 3

Alternate preparation of oxazoline-azetidinones in aqueous methanol

A suspension of 500 mg. of the thiazolidine-azetidinone, 2-benzoyl-3,3-dimethyl-7-oxo-α-[4-(benzyloxy)-phenyl]-4-thia-2,6-diazabicyclo[3.2.0]heptane-6-acetic acid, benzyl ester, in wet methanol was heated on the steam bath until solution was obtained. Mercuric acetate (600 mg.) was added to the solution and heating was continued for 10 minutes on the steam bath. The precipitate which formed was filtered through filter aid, the filtrate was evaporated to dryness in vacuo and the residue dissolved in ethyl acetate. The solution was washed with aqueous sodium bisulfite and due to the formation of an emulsion, the mixture was filtered through filter aid. The organic layer was separated from the aqueous layer and was washed with aqueous sodium bisulfite and with brine and was then dried, treated with carbon, filtered, and the filtrate evaporated to yield 447 mg. of crude oxazoline. The crude product was purified via preparative thin layer chromatography on silica gel plates employing benzene:ethyl acetate (7:3, v:v) for development and 263 mg. of purified oxazoline, 7-oxo- 3-phenyl-α-[4-(benzyloxy)-phenyl]-4-oxa-2,6-diazabicyclo[3.2.0]hept-2-ene-1-acetic acid, benzyl ester, were obtained.

EXAMPLE 4

Alternate preparation of oxazoline-azetidinone via 3-acylamino-4α-azetidin-2-one A solution of 222 mg. of 1-[α-(benzyloxycarbonyl)-4-benzyloxybenzyl]-3β-benzoylamino-4α-acetoxyazetidin-2-one in 150 ml. of methylene chloride was cooled to a temperature of about 0° C. and hydrogen chloride was bubbled into the solution until saturation was achieved. The reaction mixture was evaporated under reduced pressure and the residue dissolved in ethyl acetate. The ethyl acetate solution was washed with a dilute aqueous solution of sodium bicarbonate, was dried, and then evaporated to dryness to yield 200 mg. of 7-oxo-3-phenyl-α-[4-benzyloxyphenyl]-4-oxa-2,6-diazabicyclo[3.2.0]hept-2-ene-1-acetic acid, benzyl ester.

EXAMPLE 5

Alternative preparation of 1-[α-(benzyloxycarbonyl)-4-benzyloxybenzyl]-3β-aminoazetidin-2-one To a solution of 480 mg. (0.84 mmole) of 1-[α-(benzyloxycarbonyl)-4-benzyloxybenzyl]-3β-(α-chlorobenzylidene)amino-4α-chloroazetidin-2-one prepared as described by Example 1 in 10 ml. of dry toluene (dried by distillation over calcium hydride) were added 0.42 ml. (1.68 mmole) of tri-(n-butyl)tin hydride and 278 mg. (1.68 mmole) of azobisisobutyronitrile. The reaction mixture was stirred for 1 hour at a temperature of about 70° C. The course of the reaction was followed by TLC using benzene:ethyl acetate (9:1, v:v). After one hour the mixture was diluted with ethyl acetate and was washed successively with an aqueous solution of sodium bicarbonate, brine, and with water, was dried and treated with decolorizing carbon before being evaporated to dryness. The crude residue was triturated with petroleum ether and isopropyl alcohol.

The crude product mixture was dissolved in diethyl ether and with stirring hydrogen chloride was passed over the solution. The product, 1-[α-(benzyloxycarbonyl)-4-benzyloxybenzyl]-3β-aminoazetidin-2-one hydrochloride precipitated from solution. The ether was decanted and the product was triturated with ether. The free 3β-aminoazetidin-2-one ester was sprung from the hydrochloride salt with sodium bicarbonate. The product was purified via preparative TLC (silica gel plates, benzene:ethyl acetate, 1:1) to afford 11 mg. of the nucleus amine of the formula

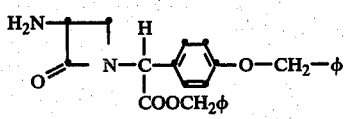

EXAMPLE 6

Alternate preparation of 1-[α-(benzyloxycarbonyl)-4-benzyloxybenzyl]-3β-aminoazetidin-2-one via p-toluenesulfonic acid salt A solution of 480 mg. (0.845 mmole) of 1-[α-(benzyloxycarbonyl)-4-benzyloxybenzyl]-3β-(α-chlorobenzylideneamino)-4α-chloroazetidin-2-one in 10 ml. of dry toluene was treated with 0.423 ml. (1.69 mmole) tri(n-butyl)tin hydride and 280 mg. (1.69 mmole) of azobisisobutyronitrile and the mixture heated at 70° C. for 1.5 hours. The 1-[α-(benzyloxycarbonyl)-4-benzyloxybenzyl]-3β-benzylideneaminoazetidin-2-one was recovered in semi-crude form from the reaction mixture. A third of the semi-crude product was dissolved in 5 ml. of ethyl acetate and 57 mg. of p-toluenesulfonic acid monohydrate were added to the solution. The solution turned dark yellow immediately. After standing at room temperature for about 20 minutes, 65 mg. of 1-[α-(benzyloxycarbonyl)-4-benzyloxybenzyl]-3β-aminoazetidin-2-one p-toluenesulfonate salt crystallized. The salt was filtered, washed with diethyl ether, and dried.

Another batch of the above p-toluenesulfonate salt was prepared with additional semi-crude deschloro 3β-benzylideneaminoazetidin-2-one and was combined with other batches of the same salt. The combined batches of tosylate salt (130 mg.) were dissolved in 5 ml. of ethyl acetate and the solution was shaken vigorously in a separatory funnel with 5 ml. of a saturated aqueous solution of sodium bicarbonate. The organic layer was separated, dried, and evaporated yielding 92 mg. of 1-[α-(benzyloxybenzyl)-4-benzyloxybenzyl]-3β-aminoazetidin-2-one.

We claim:

1. The process for preparing a 3β-aminoazetidin-2-one of the formula

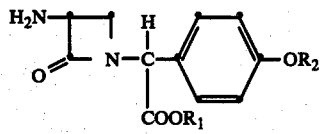

which comprises the steps of
(a) reacting the thiazolidine-azetidinone of the formula

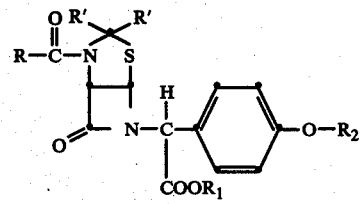

at a temperature between about 25° C. and about 100° C. with between about 2 and about 4 moles of mercuric acetate per mole of said thiazolidine-azetidinone in a water-miscible organic solvent containing between about 10 percent and about 60 percent water to form the oxazoline-azetidinone of the formula

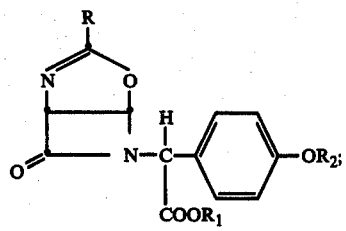

(b) reacting said oxazoline-azetidinone in an inert solvent at a temperature between about −10° C.

and about 45° C. with at least a 0.1 molar excess of a halogenating agent selected from phosphorus pentachloride, phosphorus trichloride, antimony pentachloride, and antimony trichloride in the presence of a tertiary amine to form the dichloro-3β-iminoazetidin-2-one of the formula

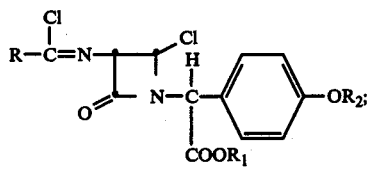

(c) heating said dichloro-3β-iminoazetidin-2-one in an inert solvent with about 2 moles per mole of said dichloroazetidin-2-one of an organo tin hydride of the formula

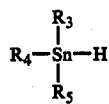

wherein $R_3$, $R_4$, and $R_5$ independently are $C_1$–$C_4$ alkyl, phenyl, or phenyl substituted by methyl or chloro, in the presence of azo-bisisobutyronitrile to form the deschloro 3β-iminoazetidin-2-one of the formula

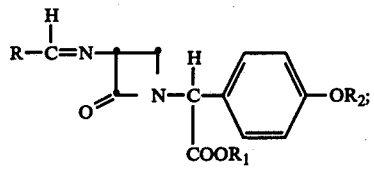

(d) hydrolyzing in the presence of an acid said 3β-iminoazetidin-2-one;
(e) recovering the salt of said 3β-aminoazetidin-2-one formed with said acid; and
(f) feeding said 3β-aminoazetidin-2-one from said salt. where in the above formulas R is $C_1$–$C_3$ alkyl, phenyl, or benzyl; both of R' are methyl or ethyl; $R_1$ is methyl, benzyl, 4-methoxybenzyl, or diphenylmethyl; and $R_2$ is benzyl, 4-methoxybenzyl, or diphenylmethyl.

2. The process of claim 1 where in step (a) the thiazolidine-azetidinone is reacted with mercuric acetate in aqueous tetrahydrofuran.

3. The process of claim 1 where in step (b) the oxazoline-azetidinone is reacted with phosphorus pentachloride.

4. The process of claim 1 where in step (c) the organo tin hydride is tri(n-butyl)tin hydride.

5. The process of claim 1 where in step (d) the 3β-iminoazetidin-2-one is hydrolyzed with p-toluenesulfonic acid monohydrate.

6. The process of claim 1 where in step (d) the 3β-iminoazetidin-2-one is hydrolyzed with aqueous hydrochloric acid.

7. The process of claim 1 wherein R is phenyl, both of R' are methyl, and $R_1$ and $R_2$ are both benzyl.

8. The process of claim 7 wherein the thiazolidine-azetidinone has the D-configuration.

* * * * *